(12) United States Patent
Kelly et al.

(10) Patent No.: US 10,871,478 B2
(45) Date of Patent: Dec. 22, 2020

(54) TRACKING EXPOSURE TO AIR POLLUTION

(71) Applicant: KONINKLIJKE PHILIPS N.V., Eindhoven (NL)

(72) Inventors: Declan Patrick Kelly, Eindhoven (NL); Michael Martin Scheja, Eindhoven (NL); Wei Chen, Eindhoven (NL); Rim Helaoui, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 322 days.

(21) Appl. No.: 16/063,573

(22) PCT Filed: Dec. 21, 2016

(86) PCT No.: PCT/EP2016/082084
§ 371 (c)(1),
(2) Date: Jun. 18, 2018

(87) PCT Pub. No.: WO2017/114710
PCT Pub. Date: Jul. 6, 2017

(65) Prior Publication Data
US 2019/0004023 A1    Jan. 3, 2019

(30) Foreign Application Priority Data

Dec. 30, 2015  (WO) ................ PCT/CN2015/099826
Jan. 26, 2016  (EP) .................................... 16152750

(51) Int. Cl.
*G01N 33/00*   (2006.01)
*G01D 9/00*    (2006.01)
(Continued)

(52) U.S. Cl.
CPC .......... *G01N 33/0075* (2013.01); *G01D 3/08* (2013.01); *G01D 9/005* (2013.01); *G01D 21/02* (2013.01)

(58) Field of Classification Search
USPC .......................................... 702/27
See application file for complete search history.

(56) References Cited

U.S. PATENT DOCUMENTS 9,377,481 B1 * 6/2016 Greenberg .............. G01P 5/001
10,139,384 B1 * 11/2018 Nourbakhsh ...... G01N 33/0062
(Continued)

FOREIGN PATENT DOCUMENTS

WO    2013039107 A1    3/2013
WO    2013063426 A2    5/2013

OTHER PUBLICATIONS

Umweltbundesamt: "Das Luftmessnetz des Umweltbundesamtes", Sep. 1, 2013, XP055285922, pp. 39, 40, 50, Fig. 17.
(Continued)

*Primary Examiner* — Paul D Lee

(57) ABSTRACT

The present application relates to a method for tracking a user's exposure to air pollutants, comprising receiving pollutant information from a plurality of air quality data sources at one or more user locations, determining a weighting for at least one of the plurality of data sources, the weighting representing quality of the pollutant information from the respective data source, selecting data sources from the plurality of data sources based on the weighting and aggregating pollutant information from the selected data sources to determine the user's exposure over a predetermined period of time.

20 Claims, 4 Drawing Sheets

(51) Int. Cl.
*G01D 21/02* (2006.01)
*G01D 3/08* (2006.01)

(56) References Cited

U.S. PATENT DOCUMENTS

| | | |
|---|---|---|
| 2005/0251339 A1 | 11/2005 | Araki |
| 2011/0037599 A1 | 2/2011 | Johnson, Jr. |
| 2012/0197852 A1* | 8/2012 | Dutta .............. H04L 67/12 707/692 |
| 2013/0144527 A1 | 6/2013 | Kuhnreichi |
| 2013/0325357 A1* | 12/2013 | Walerow ............ G01T 1/02 702/19 |
| 2014/0281479 A1 | 9/2014 | Gettings |
| 2014/0312242 A1* | 10/2014 | Valentino .......... G01P 13/00 250/395 |
| 2015/0005901 A1 | 1/2015 | Ferre |
| 2016/0091474 A1* | 3/2016 | Griffon ........... G01N 33/0036 702/24 |
| 2016/0171377 A1* | 6/2016 | Caritu ............ G06K 9/00536 706/14 |

OTHER PUBLICATIONS http://www.who.int/topics/air_pollution/en/.
http://www.honeywellanalytics.com/en/products/IAQPoint2.
http://en.wikipedia.org/wiki/IBeacon.
https://www.kickstarter.com/projects/1886143677/airair-portable-air-quality-detector.
http://www.verifone.com/media/3603729/bluetooth-low-energy-beacons-retail-wp.pdf.
http://sensaris.com/wp-content/uploads/2012/04/PM-Senspod-PM-Technical-Data-Sheet1.pdf.
Dutta et al: "Demo Abstract: Common Sense: Participatory Urban Sensing Using a Network of Handheld Air Quality Monitors", Jan. 2009 https://www.paulaoki.com/papers/sensys09-demo.pdf.

* cited by examiner

TRACKING EXPOSURE TO AIR POLLUTION

This application is the U.S. National Phase application under 35 U.S.C. § 371 of International Application No. PCT/EP2016/082084, filed on Dec. 21, 2016, which claims the benefit of International Application No. PCT/CN2015/099826 filed on Dec. 30, 2015 and International Application No. 16152750.2 filed Jan. 26, 2016. These applications are hereby incorporated by reference herein.

FIELD OF THE INVENTION

The present invention relates to tracking a user's exposure to air pollution, preferably but not exclusively to a method of tracking a user's exposure to air pollutants and an apparatus for tracking a user's exposure to air pollutants.

BACKGROUND OF THE INVENTION

It is well established that prolonged exposure to many types of air pollution correlates to an increased risk of major disease and increased death rates. Since it is not possible to entirely avoid exposure to air pollution, many governmental bodies publish time-averaged threshold values which define the limits of acceptable exposure. For example, Chinese standard GB3095-2012 mandates a level of 35 µg/m3 for fine particulate matter $PM_{2.5}$ over a 24 hour period, while the World Health Organisation WHO Air Quality Guidelines set a limit value for $PM_{2.5}$ as 10 µg/m3 as an annual mean and 25 µg/m3 as a 24 hour mean. Other pollutants such as O3 and NO2 have average exposure levels set over a variety of different periods: for example the WHO Guidelines set a value for O3 exposure as 10 µg/m3 as an 8 hour mean, while NO2 exposure is set at 40 µg/m3 as an annual mean, but 200 µg/m3 as a 1 hour mean.

Real-time (or near real-time) air quality information is increasingly publically available based on data from environmental monitoring stations which are typically set up and operated by government agencies, often to assist in complying with environmental legislation. For example, the website at http://aqicn.org publishes real-time air quality information for various world cities, including pollutant levels at specific sensor sites within those cities. Although high quality data is available from public monitoring stations, the spatial coverage from these stations is relatively low and the uncertainty of pollution concentration increases with increasing distance from a monitoring station. To increase the coverage, other connected sensors can be used and their data broadcast publicly.

For example, air quality sensors are increasingly found in other locations, for example in commercial buildings, where they are typically used for demand controlled ventilation, and in private homes, where air purifiers are beginning to appear. Such air purifiers may have integrated sensors which can send their data to an app installed on a user's device, such as a smart phone.

However, in contrast to environmental monitoring stations, the quality of data provided by other sources cannot be guaranteed. For example, for sensors integrated into commercial air purification systems, the quality of the data is likely to depend on the manufacturer, brand and model. Similarly, people with wearable sensors may broadcast the air quality measurement, but the results will strongly depend on the position of the sensor and the sensor quality.

There is therefore a general problem that in cases where air pollution data is shared, the quality of the data is unknown and cannot be guaranteed.

US2015/005901 discloses establishing a sensor registry for a plurality of sensor devices and assigning a quality rating to such devices by cross-checking the consistency of readings with other devices in a similar location.

Even if it is possible to check air quality values at various specific locations based on publicly available air quality data, it is very difficult for a person to determine their personal exposure to ensure that this falls within the published guideline limits. This becomes even more difficult as the person moves through different indoor and outdoor locations which are usually characterised by their own pollutant profiles and concentrations.

For specific target groups, such as those with respiratory disease, tracking exposure is essential to prevent disease exacerbation.

The document of the Umweltbundesamt: "Das Luftmessnetz des Umweltbundesamtes", 1 Sep. 2013, discloses a method for tracking human's exposure to air pollutants with a plurality of EMEP (European Monitoring and Evaluation Programme) environmental monitoring stations operated by the Umeweltbundesamt and co-operation partners.

SUMMARY OF THE INVENTION

It is an object of the invention to provide a method and apparatus for tracking a user's exposure to air pollutants which substantially alleviates or overcomes one or more of the problems mentioned above.

The invention is defined by the independent claims. The dependent claims define advantageous embodiments.

According to the present invention, there is provided a method for tracking a user's exposure to air pollutants, comprising receiving pollutant information from a plurality of air quality data sources at one or more user locations, determining a weighting for at least one of the plurality of data sources, the weighting representing quality of the pollutant information from the respective data source, selecting data sources from the plurality of data sources based on the weighting and aggregating pollutant information from the selected data sources to determine the user's exposure over a predetermined period of time.

By aggregating accurate and reliable pollutant information over a predetermined period, users are able to compare their personal exposure with published threshold values.

The method may advantageously comprise selecting the data source having the highest weighting as representing the most accurate data. By selecting the highest weighting over a number of data sources, the overall inaccuracy in the aggregated exposure figures can be kept as low as possible.

The method may further comprise calculating an average value for a pollutant level from pollutant information from data sources having equal weighting. Where multiple data sources are allocated the same weighting, an average level may be calculated which may improve accuracy.

The method may comprise not selecting data sources having a weighting below a predetermined threshold. In other words, the method may comprise only selecting data sources having a weighting above a predetermined threshold. Advantageously, air quality data that is deemed to be unreliable can be excluded from the exposure calculations.

Determining the weighting for at least one of the plurality of data sources may comprise receiving predetermined weighting information. Advantageously, the method may reuse previously determined weighting information, so avoiding the need for recalculation. The predetermined weighting information may also be more reliable, since it may have been calculated from a number of different measurements.

The predetermined weighting information may be obtained by receiving identification information for the at least one data source, transmitting the identification information to a remote server and receiving the predetermined weighting information for the at least one data source corresponding to the identification information.

For example, where each sensor associated with a data source has a unique id, that unique id can be transmitted by the sensor and used by the user, for example by an app on a user's mobile device, to retrieve weighting information for that sensor, for example from a cloud based service.

In turn, when a sensor has a new weighting calculated, that weighting, together with the unique id, can be uploaded by the user to the remote server, for example, the cloud based service, so that it can be subsequently used by other devices. By uploading weightings to a remote server, a consensus weighting can in time be achieved based on weightings of a large number of users.

Advantageously, determining the weighting for at least one of the plurality of data sources may comprise determining the weighting of the data source based on information about the type of data source, such as the sensor model of a sensor associated with the data source. Since units of the same sensor model are likely to be built to the same standards and so have similar data accuracy and reliability, weightings can be assigned to such models without the need to make individual comparisons with known standard sensors.

To establish weightings based on a sensor type or model, the method may comprise comparing pollutant information for each of a plurality of different sensors having the same sensor type with pollutant information from predetermined data sources associated with high quality pollutant information, calculating a degree of sensor quality for the sensor type, the degree of sensor quality being associated with a weighting, and assigning a weighting to a given sensor type based on the calculated degree of sensor quality.

Advantageously, determining the weighting of a data source may comprise comparing first pollutant information from an unweighted data source with second pollutant information from a predetermined data source that is associated with high quality pollutant information and assigning a weighting to the unweighted data source based on a result of the comparison.

The unweighted data source is therefore effectively compared with a standard source so that its weighting can be accurately determined. The predetermined data source may be an environmental monitoring station which is known or certified to produce high quality data. Once the unweighted data source has been compared against the standard, it may itself be used as a standard data source to classify further unweighted data sources, thereby establishing a network of data sources whose quality has been measured against each other.

Pollutant information can therefore be collected from the user's surroundings while leveraging a pool of sensors with high spatial coverage, the quality of which has been verified against other known high quality data sources.

The weighting for an unweighted data source may be determined based on the distance between the unweighted data source and the predetermined data source. For example, a secondary sensor within a first predetermined radius of a primary sensor (for example, a known environmental monitoring system) may be weighted at the same weighting as the primary sensor if its air quality data matches the data of the primary sensor to within a given threshold. Where the secondary sensor lies within a second predetermined radius further than the first predetermined radius, the weighting may be lowered to reflect the uncertainty due to the increased distance from the primary sensor.

The method may further comprise receiving supplementary information regarding the environment around the unweighted data source to determine whether the first pollutant information is valid. For example, where a sensor lies indoors, the validity of its readings relative to a nearby outdoor sensor may depend on whether a window to the outside is open. Where supplementary information regarding the state of the window is provided, this information can be used to determine whether the readings are comparable. Other types of supplementary environmental information are envisaged, for example temperature or humidity information which can indicate whether two sensors are in the same environment. Advantageously, aggregating the pollutant information may comprise determining, for each of a plurality of locations, a pollutant concentration from the pollutant information, determining the duration of the exposure to the pollutant concentration and summing over the plurality of locations. This allows for an overall exposure to be calculated and displayed to the user.

The exposure may be calculated for each of a plurality of segments where the pollution concentration is deemed to remain constant within a segment, so potentially simplifying the calculation of the exposure.

The exposure calculation may also take account of a breathing rate of a user, determined for example from a fitness monitoring application, or a heart rate sensor. By monitoring the breathing/respiration rate of a user while he is exposed to pollutants, a more accurate estimation of the user's pollutant exposure can be performed. The data gathered by a breathing sensor may be used by the method for tracking a user's exposure to air pollutants to increase its accuracy.

According to an embodiment of the invention, the method for tracking a user's exposure to air pollutants further comprises a step of determining the breathing rate of a subject/user. In this step, it is determined how much air (volume) is being inhaled the user. In this embodiment, the step of aggregating the pollutant information further comprises taking into account the breathing rate data and determining the impact of the exposure to air pollutants to the subject/user by also using this breathing rate data.

Where a sensor provides an average pollutant concentration for a given time period, for example for each hour, the pollutant concentration for the time of exposure may be determined by subsequently looking up the pollutant concentration at the relevant time, for example on a public source such as the Internet.

It will be understood by the skilled person that the described method may be performed by a computer program, for example an app running on a mobile device, e.g. a smartphone capable of tracking the movement of a user with a GPS chip. The computer program, when executed by a processor of a device, is arranged to perform the described method.

Other devices such as a breathing sensor or other body condition sensors may be used to further increase accuracy of the determination of the exposure of the user to pollutants over time.

According to a further aspect of the invention, there is provided an apparatus for tracking a user's exposure to air pollutants, comprising a receiver configured to receive pollutant information from a plurality of data sources at one or more user locations and a processor, the processor being configured to determine a weighting for each of the plurality of data sources, the weighting representing quality of the pollutant information from the respective data source and to select pollutant information from the plurality of data sources based on the weighting, the processor being further configured to aggregate pollutant information from the selected data sources to determine the user's exposure over a predetermined period of time.

According to an embodiment of the invention, the receiver is further configured to receive a respiration rate of the user and the processor is further configured to determine the user's exposure taking into account the respiration rate. Taking into account the respiration rate further increases the accuracy of the determination of the user's exposure.

The apparatus may be a mobile device such as a smartphone running an app. Alternatively, the apparatus may be a dedicated pollution monitor, using a combination of hardware and software to implement its functionality.

By providing an apparatus which can aggregate pollution information over any given time period, which may be user programmable, a user can compare their exposure with published exposure limit information.

The apparatus may comprise a GPS module configured to provide location data to be associated with pollutant information at a given location. The GPS module can advantageously be used to determine distance from a data source.

The apparatus may further comprise a body condition sensor for providing data on the body condition of the user to the apparatus. The body condition sensor may be a breathing sensor capable of sensing the amount of air that is inhaled by the user. This increases the accuracy of the determination of the exposure of the user to pollutants. Such a breathing sensor may be wirelessly coupled to the apparatus.

The receiver may comprise a short range receiver configured to receive pollutant information being broadcast by a data source. It may also be configured to receive body condition data, e.g. respiration rate, of the user. For example, the short range receiver may be a Bluetooth or Low Power Bluetooth receiver or may receive communications via any other communication protocol, including Wifi, Zigbee and so on. The apparatus may comprise an NFC Near Field Communication system for obtaining data from a sensor when proximate to the sensor.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
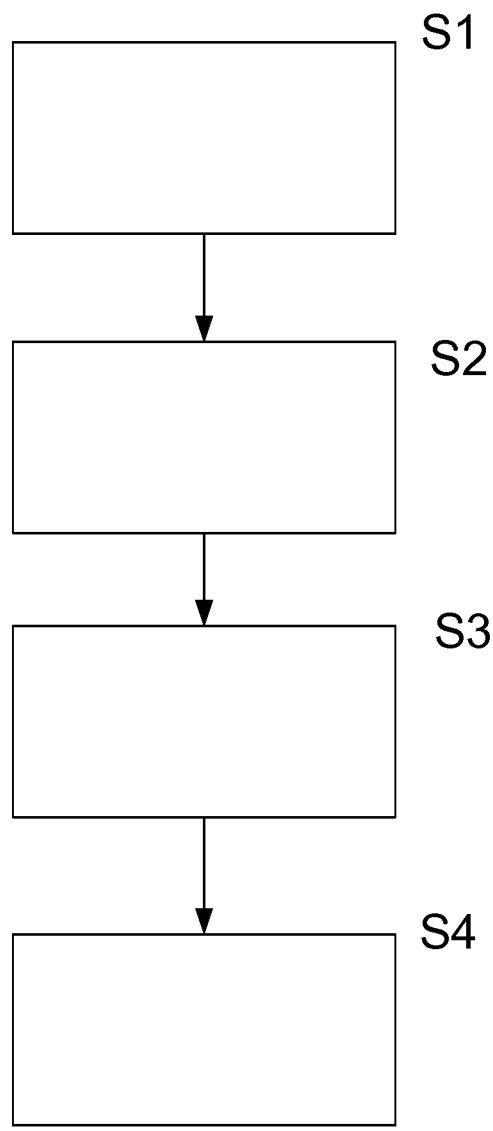
FIG. 1 shows a flowchart setting out the sequence of steps carried out to determine user exposure in accordance with an embodiment.

Referring to FIG. 1, a method for determining a user's exposure to air pollutants is described and broadly comprises receiving pollutant information (s1) from a plurality of air quality data sources at one or more user locations, determining a weighting (s2) for at least one of the plurality of data sources, the weighting representing quality of the pollutant information from the respective data source, selecting data sources (s3) from the plurality of data sources based on the weighting and aggregating pollutant information (s4) from the selected data sources to determine the user's exposure over a predetermined period of time.

Numerous different weighting schemes can of course be used. In this disclosure, an exemplary weighting scheme assigns a weighting range between 0 and 5. A weighting of 5 is given to data sources which are of very high quality, for example environmental monitoring stations providing data obtained from state-of-the-art professional devices, such as Beta Attenuation Monitors (BAM) for $PM_{2.5}$ monitoring. At the other end of the scale, 0 represents unreliable data which can be ignored by the system during exposure estimation. Commercial data sources, for example, sensors used in commercial buildings, may be assigned a weighting of 4. It is not necessarily the case that a user's own sensors at home, which may be intrinsically less reliable than commercial sensors, should be given a lower rating. In general, there will be no overlap between home sensors and commercial sensors, so that these sensors can be given equal weight with commercial sensors. A user's own personal wearable sensors will in general be more trusted than other sources.

Figure 2:
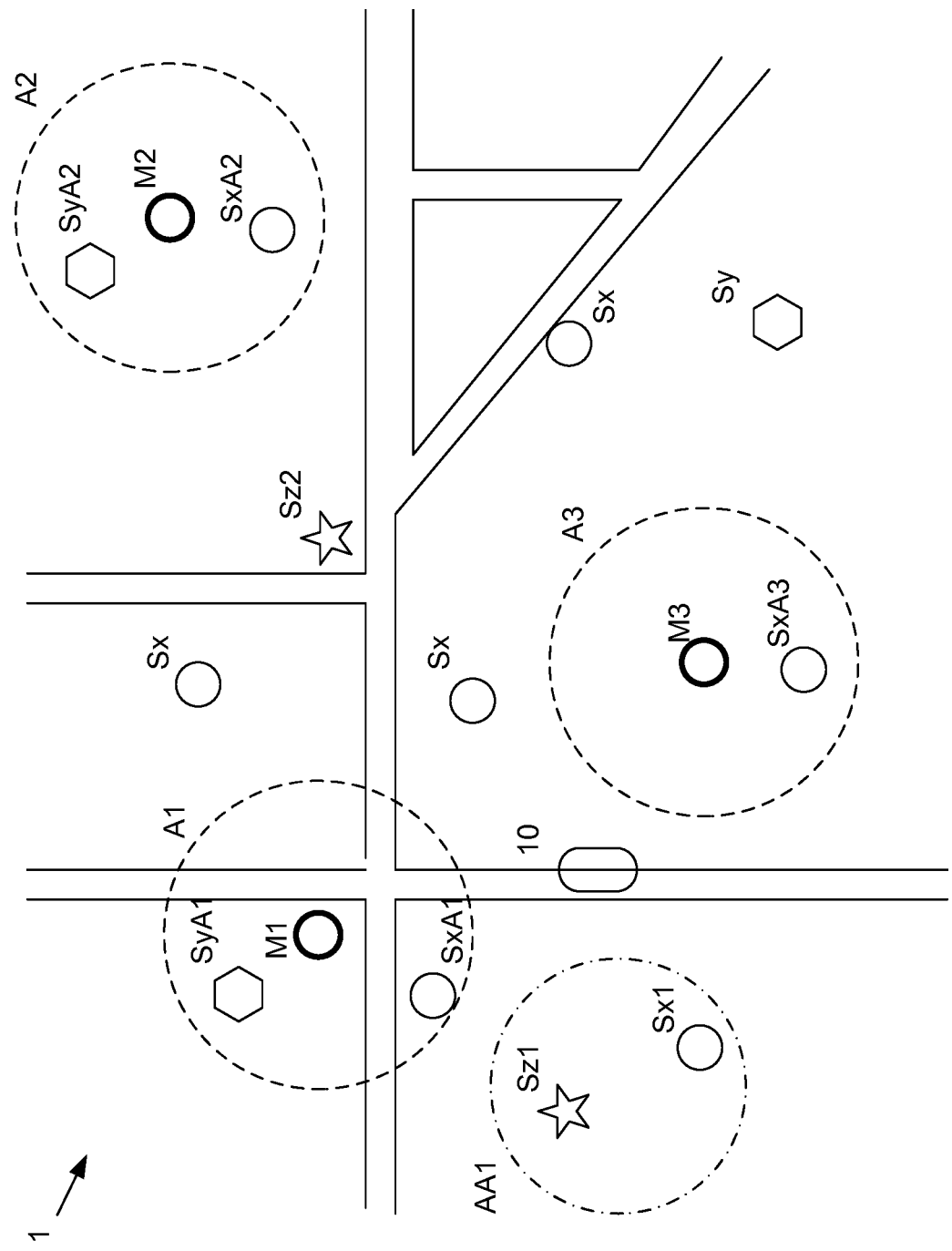
FIG. 2 shows a map schematically showing the positions of a plurality of different types of sensor.

FIG. 2 is a schematic map showing the positions of a plurality of sensors. It is used to demonstrate how sensor weightings can be determined.

Referring to FIG. 2, a plurality of sensors M1-Mn, Sx, Sy, Sz are shown on a schematic map 1 together with a user device 10 which runs a program or app 11 (shown in FIG. 3) for performing exposure tracking. A first plurality of sensors M1, M2, . . . , Mn represent environmental monitoring stations, for example operated by a government agency, that provide high quality information about air quality, for example, values for common pollutants such as $PM_{2.5}$, $PM_{10}$, $NO_2$, $O_3$ and so on. This information may be broadcast and displayed via, for example, the Internet. The information may also be broadcast or otherwise transmitted locally, so that a user device 10 is able to receive the broadcasts using any appropriate technology, including by text, Wifi, Bluetooth, Low Energy Bluetooth, Zigbee, iBeacon, NFC and so on. For example, a Wifi scanner program on the mobile device receives air quality information from a variety of sensors, together with a power index of the signal. The power index can be used as an indicator of the distance of the user to the Wifi device. If multiple signals are received, then a geometrical reconstruction of the Wifi locations can be used to triangulate the position of the sensor. The sensor information may be encrypted, using for example public/private key encryption so that the recipient can verify that a signal actually comes from a claimed sensor type.

A second plurality of sensors Sx, Sy, Sz are shown. The labels Sx, Sy, Sz represent different types or models of sensor. For example, Sx represents different sensor units in different locations but all being the same sensor model. These sensors represent sensors that are found in commercial premises, private households and the like, integrated into connected air purifiers, connected sensor boxes or connected stand-alone sensors for specific pollutants. Each sensor type is characterised by its specific quality properties such as accuracy, reliability, inter-sensor variation, limit of detection and the like.

The pollutant concentrations within a close radius (e.g. 50-500 m) of first sensors M1, M2, M3 at an environmental monitoring station, illustrated by the dotted circles A1, A2, A3 in FIG. 2, are assumed to be homogenous. Therefore, a pollutant concentration provided by a second sensor SxA1 located within this radius in area A1 should show the same concentration as the one obtained from the environmental monitoring station M1. Good agreement between the data from the two sensors M1, SxA1, for example, agreement to within a few percent, indicates a good quality of the corresponding sensor model X. Poor quality data is indicated in cases where the values from those two sensors differ significantly.

However, differences in the sensor environment and location need to be taken into account. The second sensor SxA1 may be located, for example, in a sensor box on a balcony, so it would be exposed to outside air. If, on the other hand, the second sensor SxA1 is located indoors, it would be expected that the sensor values would differ significantly. In this case, supplementary information may be made available which would indicate whether, for example, the windows are currently open. For example, temperature or humidity information might be broadcast, and analysis of this supplementary information would indicate whether the windows are open, and therefore whether a comparison between the air quality information provided by the first and second sensors is valid.

Where sensor units Sx based on the same sensor model X exist in sufficient proximity to the environmental monitoring stations M1-$n$, a degree of sensor quality D for the sensor model X can be defined using following relationship:

$$D = \frac{\overline{M} - \overline{S_x}}{\overline{M}}$$

where $$\overline{S_x} = \frac{S_x A_1 + S_x A_2 + S_x A_3 + \cdots S_x A_n}{n}$$

and $$\overline{M} = \frac{M_1 + M_2 + M_3 + \cdots M_n}{n}$$

Here, M1, M2 and M3 are data obtained from the environmental monitoring stations shown in FIG. 2. $S_X A1$, $S_X A2$ and $S_X A3$ are data obtained from sensors of the model X located in areas A1, A2 and A3. The bar above the letter M and the letter S indicate mean values.

The same approach can be used to calculate the degree of sensor quality D for the other sensor models Sy and Sz.

In order to assign a weighting W to the newly assessed sensors, the following relationships can, as an example, be applied:

TABLE 1

| Weighting | D |
|---|---|
| 5 | $|D| \leq 0.1$ |
| 4 | $0.1 < |D| \leq 0.2$ |
| 3 | $0.2 < |D| \leq 0.3$ |
| 2 | $0.3 < |D| \leq 0.4$ |
| 1 | $|D| > 0.4$ |

A weighting can therefore be applied to a sensor model, so that sensors Sx which are not within areas A1, A2 or A3 are still associated with a particular weighting to indicate the accuracy of the data from those sensors. For example, this may apply to the sensor labelled Sx1 in FIG. 2. It will be understood that the same principles apply to assigning weighting to a large number of different sensor models, although only three are shown in the Figure.

Referring again to FIG. 2, where a sensor Sz1 is not in proximity to a known high quality data source such as an environmental monitoring station M1, the sensor can still be given a weighting by reference to the weighting given to another sensor. For example, in FIG. 2, the sensors Sx1, Sz1 might be expected to be in sufficiently close proximity to provide the same reading, as indicated by the dotted area AA1. Therefore, a comparison may be carried out between the pollutant information from sensors Sz1 and Sx1 and if they match to within a predetermined threshold, then the sensor Sz1 may be given the same weighting as the sensor Sx1, which has a weighting by virtue of it being of model type X.

The process by which sensor weightings can be assigned is now described with reference to FIG. 3.

Figure 3:
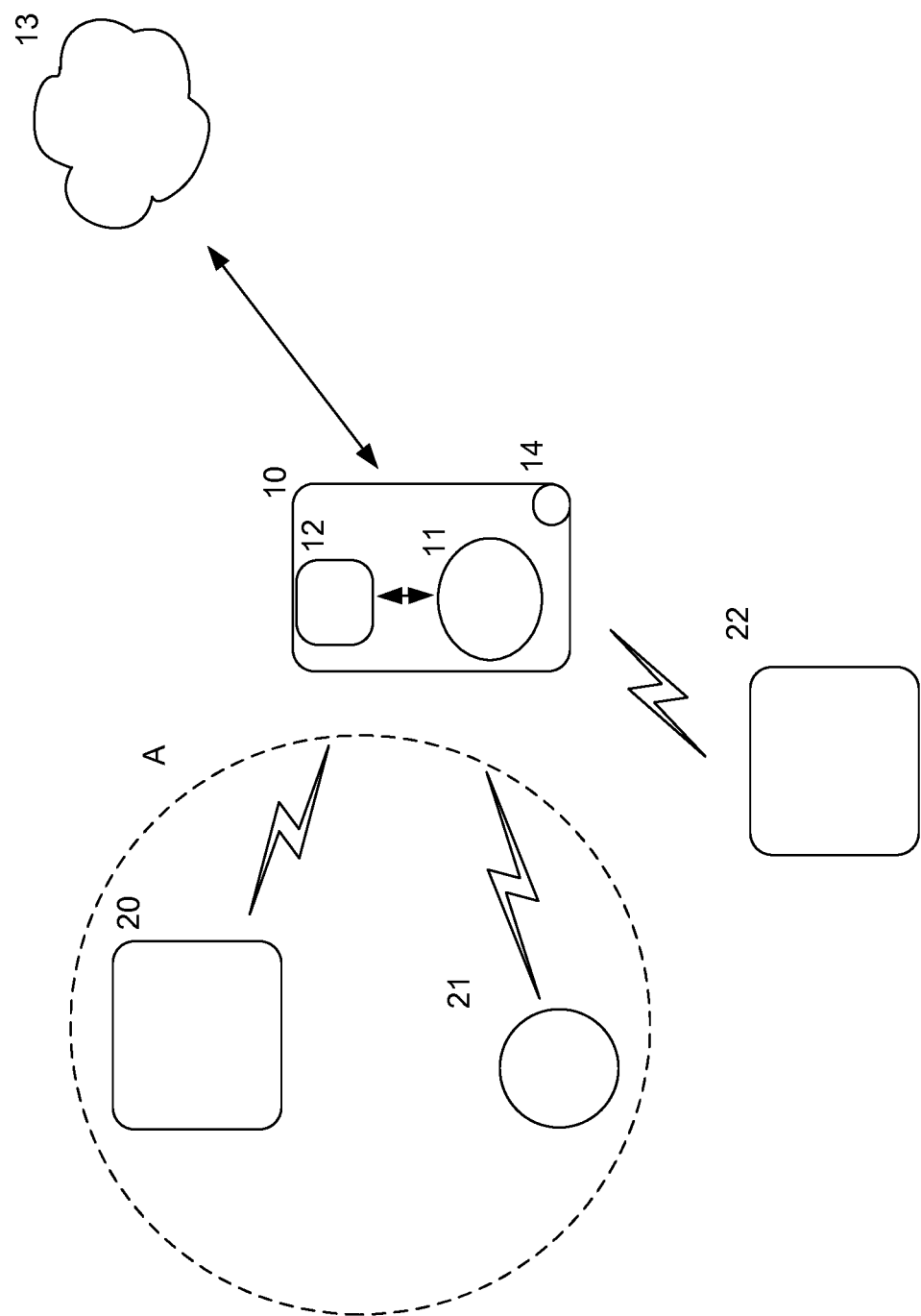
FIG. 3 shows a system according to an embodiment.

Referring to FIG. 3, a program or app 11 running on the processor 12 of a mobile device 10 receives information from a plurality of sensors 20, 21, 22. The information comprises, for example, pollutant data including pollutant type, value and units of measurement, GPS coordinates of the sensor, the timestamp of the data point and the sampling duration (for example, for 1 hour averages), the sensor type, for example manufacturer and model, sensor id, and any other sensor properties, for example expected variation in the pollutant level. It will be understood that not all the fields are essential and that they depend on the type of sensor. At a minimum a sensor may just indicate the pollutant value (assuming a unit of measurement). The app 11 checks whether any of the connected sensors are trusted sensors. For example, the first sensor 20 may indicate via its sensor id that it is an environmental monitoring station (M1) and is therefore a trusted sensor. The app 11 assigns this sensor 20 a weighting of 5. Alternatively, the app 11 checks the sensor id via a remote server system, for example a cloud based service 13, and this service informs the app 11 that the first sensor 20 is an environmental monitoring station. In a further alternative embodiment, the sensor model information is used to check for a weighting via the cloud based service 13.

As an example, assuming that the first sensor 20 is a trusted sensor and that predetermined weighting information is not available for the second sensor 21, the app 11 receives GPS information from the first and the second sensors 20, 21. From this information, the app 11 determines that the sensors 20, 21 lie within substantially the same area A. As a result, the app 11 compares the pollutant level information of the first and second sensors. If these match to within a predetermined threshold, the app 11 assigns the same weighting as the first sensor 20 to the second sensor 21.

The third sensor 22 may be, for example, a wearable or mobile sensor. The sensor id or sensor model, if available, may be checked against the records held at the cloud service 13 to determine if weighting information is available. If no such information is available, and the third sensor 22 is not close enough to a reliable data source to perform a comparison of pollutant information, or if such a comparison shows a poor match, then a low weighting may be assigned.

It will be understood by the skilled person that the process of checking and assigning weightings to sensors may be a continuous one performed by a large number of devices as they travel around a map, in a crowdsourcing manner. Feedback from all of the devices may be taken into account to provide weightings for all the sensors in a geographical area, so building up a map of weighted sensors at a remote server (or cloud based service) 13.

The process of tracking a user's personal exposure will now be described with reference to FIG. 4.

Figure 4:
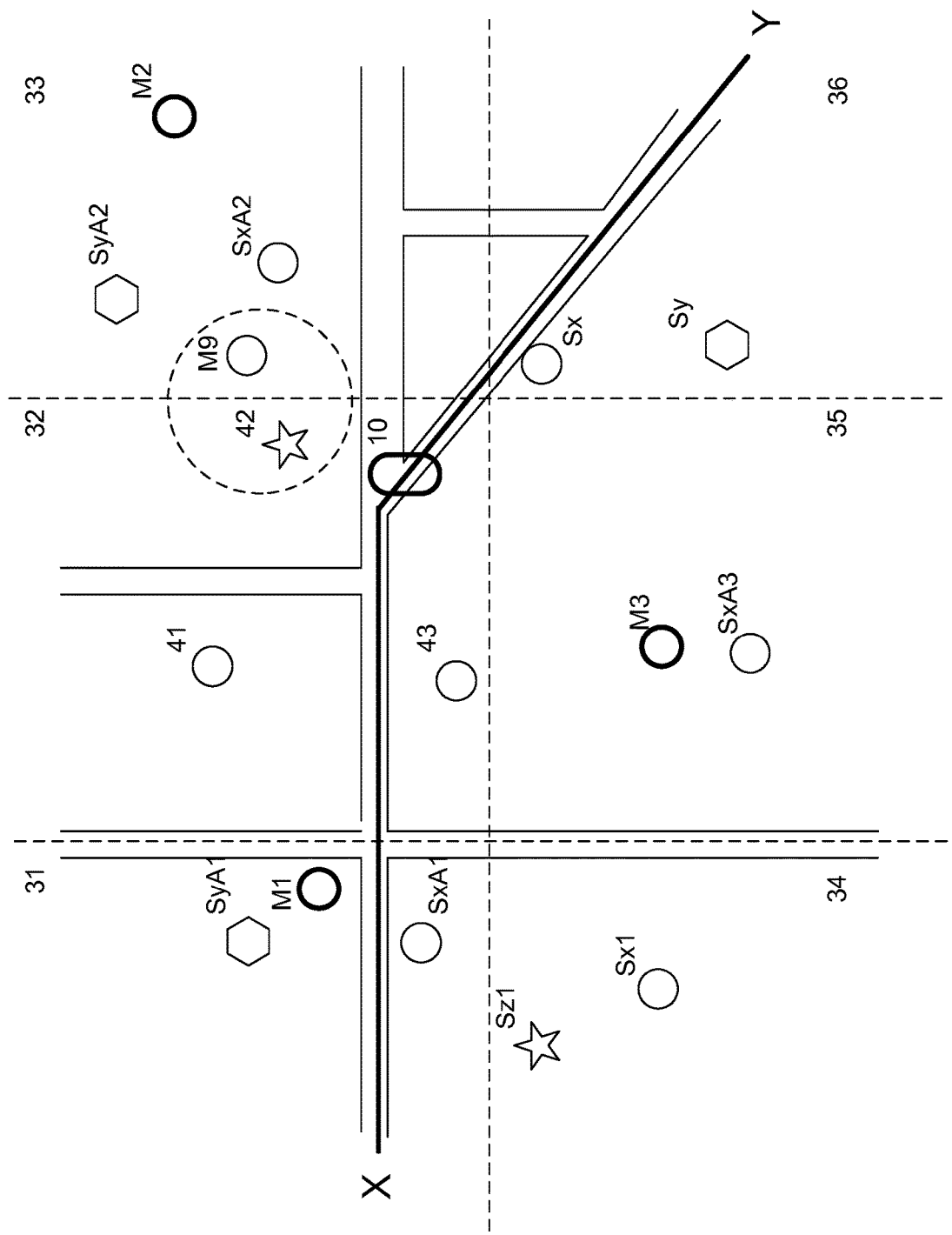
FIG. 4 shows a map divided into segments to allow exposure tracking according to an embodiment.

FIG. 4 shows a map similar to that of FIG. 2 divided into a plurality of segments 31 to 36. Each segment is associated with one or more sensors. Certain segments may not have any sensors within them. A user device 10 moves between points X and Y on the map passing, for example, through segments marked 31, 32, 33, 36. The principle of tracking a user's exposure to air pollution is that for each segment, it is assumed that the pollutant concentration is uniform throughout the segment. In an embodiment, it is first determined which segment the user's mobile device 10 occupies, for example based on GPS data from a GPS module 14 within the mobile device (shown schematically in FIG. 3). Sensors lying within the same segment are then determined, again based on GPS data, or based on a determination that the sensor is relatively close, for example because the sensor data is available over a short range communication protocol such as Bluetooth.

The user's device 10 receives a plurality of signals from the sensors lying within the same segment. For example, when the user device 10 is within the second segment 32, it is determined that three sensors 41, 42 and 43 are within the segment. The weightings for each of the sensors are determined, for example, by transmitting the received sensor ids to a remote server and receiving predetermined weighting information from the remote server, as shown in FIG. 3. In an alternative embodiment, the weighting information can be determined on the fly by using the techniques set out above. For example, where it is determined that an unclassified sensor 42, for example a mobile or wearable sensor within the same segment as the user device 10 is proximate to an environmental monitoring station M9 (which need not be within the same segment), the pollutant information from the unclassified sensor 42 and the station M9 can be compared to determine a weighting to be given to the unclassified sensor 42.

Once the weightings for each sensor within the segment are known, the sensors with the highest weightings are selected to provide pollutant concentration information. For example, where one sensor has a higher weighting than any other sensor, pollutant information from that sensor is used by the exposure tracking app 11. Where multiple sensors have the same highest weighting, the pollutant concentration information from each sensor may be averaged.

Where there is no available sensor within a given segment, data from sensors in adjacent segments may be used, again based on the highest weighting information. Additional weighting factors may be considered based on the distance between the user device and the sensors in the neighbouring segments, again based on GPS data or other calculations.

In an alternative embodiment, the segments are centred on the user's GPS position and only sensors lying within a predetermined radius are taken into account, again based on sensor GPS or short range communication data.

Referring again to FIG. 4, as a user moves from X to Y, their mobile device 10 records both their location and the time spent within the segment. The concentration of the pollutant is also known as described above, by receiving that data from the most highly weighted data source. The exposure in each segment can therefore be calculated by:

Time spent within segment*pollutant concentration within the segment per unit time      Equation 1

This is done for each segment crossed and the total sum is used as the total exposure.

The calculation can be further enhanced by taking into account factors such as the user's breathing rate, determined for example from fitness applications, estimated from heart rate measurements and so. In this case the exposure is calculated by the equation:

Time spent within segment*pollutant concentration within the segment per unit time*breathing rate      Equation 2

It will be appreciated by the skilled person that the calculations above depend on how the pollutant concentration is presented. For example, where the pollutant concentration is presented as an average exposure for a preceding one hour period, then if the user has spent 20 minutes within the segment, their exposure can be calculated as one third of that cited exposure. Certain data sources maintain historical exposure data. Since the exposure data given for a preceding period is in fact out of date when a user is within the segment, a more accurate estimate for data from such sources may be obtained by retrieving the exposure data at a later point in time, for example one hour later, using the sensor's unique id to retrieve the data, for example, over the Internet.

It will be understood by the skilled person that the described method of exposure tracking can be implemented as a program or an app on a mobile device such as but not limited to a smartphone or tablet, or on a dedicated pollution measuring device. The hardware and software requirements for implementing the method on a smart device or dedicated device are well understood by the skilled person.

The above embodiments as described are only illustrative, and not intended to limit the technique approaches of the present invention. Although the present invention is described in detail referring to the preferable embodiments, those skilled in the art will understand that the technique approaches of the present invention can be modified or equally displaced without departing from the spirit and scope of the technique approaches of the present invention, which will also fall into the protective scope of the claims of the present invention. In the claims, the word "comprising" does not exclude other elements or steps, and the indefinite article "a" or "an" does not exclude a plurality. Any reference signs in the claims should not be construed as limiting the scope.

The invention claimed is:

1. A method for tracking a user's exposure to air pollutants, the method comprising:
   receiving pollutant information from a plurality of air quality data sources at one or more user locations;
   determining a weighting for each of the plurality of air quality data sources, the weighting representing quality of the pollutant information from the respective data source;
   selecting data sources from the plurality of air quality data sources based on the weighting, wherein the selected data sources have a weight that is greater than a predetermined threshold; and
   aggregating pollutant information from the selected data sources to determine the user's exposure over a predetermined period of time.

2. The method of claim 1, comprising selecting from the plurality of air quality data sources an air quality data source having the highest weighting as representing the most accurate data.

3. The method of claim 1, further comprising calculating an average value for a pollutant level from pollutant information from data sources having equal weighting.

4. The method of claim 1, wherein determining the weighting for at least one of the plurality of air quality data sources comprises receiving predetermined weighting information.

5. The method of claim 4, further comprising:
receiving identification information for at least one of the plurality of air quality data sources;
transmitting the identification information to a remote server; and
receiving the predetermined weighting information for the at least one of the plurality of air duality data sources corresponding to the identification information.

6. The method of claim 1, wherein determining the weighting for at least one of the plurality of air quality data sources comprises calculating the weighting of the at least one of the plurality of air quality data sources based on information about a type of data source.

7. The method of claim 6, wherein each of the data sources comprises a sensor, the method comprising comparing pollutant information for each of a plurality of different sensors having a same sensor type with pollutant information from predetermined data sources (Mn) associated with high quality pollutant information;
calculating a degree of sensor quality for the sensor type, the degree of sensor quality being associated with a weighting; and
assigning a weighting to a given sensor type based on the degree of sensor quality.

8. The method of claim 1, wherein determining the weighting of a data source comprises:
comparing first pollutant information from an unweighted data source with second pollutant information from a predetermined data source (Mn) that is associated with high quality pollutant information; and
assigning a weighting to the unweighted data source based on a result of the comparing the first pollutant information from an unweighted data source with second pollutant information.

9. The method of claim 8, comprising determining a weighting for the unweighted data source based on a distance between the unweighted data source and the predetermined data source (Mn).

10. The method of claim 8, comprising receiving supplementary information regarding an environment around the unweighted data source to determine whether the first pollutant information is valid.

11. The method of claim 1, wherein aggregating the pollutant information comprises:
determining, for each of a plurality of positions, a pollutant concentration from the pollutant information, determining a duration of the user's exposure to the pollutant concentration and summing over the plurality of positions.

12. The method according to claim 1, further comprising determining a respiration rate of the user and wherein the determination of the user's exposure over a predetermined period of time is done by further taking into account the respiration rate of the user.

13. An apparatus for tracking a user's exposure to air pollutants, the apparatus comprising:

a receiver configured to receive pollutant information from a plurality of data sources at one or more user locations;
a processor; and
a tangible non-transitory computer-readable medium that stores instructions,
which when executed by the processor, cause the processor to: to determine a weighting for each of the plurality of data sources, the weighting representing quality of the pollutant information from the respective data source; select data sources from the plurality of data sources based on the weighting, wherein the selected data sources have a weight that is greater than a predetermined threshold; and aggregate pollutant information from pollutant information from the selected data sources to determine the user's exposure over a predetermined period of time.

14. The apparatus for tracking a user's exposure to air pollutants according to claim 13, wherein the receiver is further configured to receive a respiration rate of the user and wherein the processor is further configured to determine the user's exposure by taking into account the respiration rate.

15. The apparatus for tracking a user's exposure to air pollutants according to claim 13, further comprising a respiration rate detector.

16. The apparatus for tracking a user's exposure to air pollutants according to claim 13, wherein the instructions, when executed by the processor further cause the processor to select the data sources having the highest weighting as representing the most accurate data.

17. The apparatus for tracking a user's exposure to air pollutants according to claim 13, wherein the instructions, when executed by the processor further cause the processor to calculate an average value for a pollutant level from pollutant information from data sources having equal weighting.

18. The apparatus for tracking a user's exposure to air pollutants according to claim 13, wherein the instructions, when executed by the processor further cause the processor to receive predetermined weighting information when determining the weighting for at least one of the plurality of data sources.

19. The apparatus for tracking a user's exposure to air pollutants according to claim 18, wherein the instructions, when executed by the processor further cause the processor to:
receive identification information for at least one of the plurality of data sources;
transmit the identification information to a remote server; and
receive the predetermined weighting information for the at least one of the plurality of data sources corresponding to the identification information.

20. The apparatus for tracking a user's exposure to air pollutants according to claim 13, wherein the instructions, when executed by the processor further cause the processor to calculate the weighting of the data source based on information about a type of data source when determining the weighting for at least one of the plurality of data sources.

* * * * *